US010387301B2

(12) United States Patent
Goldman et al.

(10) Patent No.: US 10,387,301 B2
(45) Date of Patent: Aug. 20, 2019

(54) HIGH-CAPACITY STORAGE OF DIGITAL INFORMATION IN DNA

(71) Applicants: Nick Goldman, Royston (GB); John Birney, London (GB)

(72) Inventors: Nick Goldman, Royston (GB); John Birney, London (GB)

(73) Assignee: European Molecular Biology Laboratory, Heidelberg (DE)

( * ) Notice: Subject to any disclaimer, the term of this patent is extended or adjusted under 35 U.S.C. 154(b) by 644 days.

(21) Appl. No.: 14/556,213

(22) Filed: Nov. 30, 2014

(65) Prior Publication Data

US 2015/0261664 A1 Sep. 17, 2015

Related U.S. Application Data

(63) Continuation of application No. PCT/EP2013/061300, filed on May 31, 2013.

(60) Provisional application No. 61/654,295, filed on Jun. 1, 2012.

(51) Int. Cl.
| | |
|---|---|
| *G06N 3/12* | (2006.01) |
| *B82Y 10/00* | (2011.01) |
| *G06F 12/02* | (2006.01) |
| *G16B 30/00* | (2019.01) |
| *G16B 50/40* | (2019.01) |
| *G16B 50/50* | (2019.01) |

(52) U.S. Cl.
CPC ............ *G06F 12/023* (2013.01); *B82Y 10/00* (2013.01); *G06N 3/123* (2013.01); *G16B 30/00* (2019.02); *G16B 50/40* (2019.02); *G16B 50/50* (2019.02); *G06F 2212/1032* (2013.01)

(58) Field of Classification Search
None
See application file for complete search history.

(56) References Cited

U.S. PATENT DOCUMENTS

| 6,312,911 B1 | 11/2001 | Bancroft et al. |
| 2005/0053968 A1 | 3/2005 | Bharadwaj et al. |

FOREIGN PATENT DOCUMENTS

| GB | 2 376 686 | 12/2002 |
| JP | 2005-055900 | 3/2005 |
| JP | 2005-072772 | 3/2005 |
| JP | 2006-522356 | 9/2006 |
| RU | 106771 U1 | 7/2011 |
| WO | 03/025123 | 3/2003 |
| WO | 2014/014991 | 1/2014 |

OTHER PUBLICATIONS

Tian et al. Advancing high-throughput gene synthesis technology Molecular Biosystems vol. 5, pp. 714-722 (Year: 2009).*
Thornton et al. Automation and validation of DNA-banking systems Drug Discovery Today vol. 10, pp. 1369-1375 (Year: 2005).*
Ailenberg, M. & Rotstein, O. D. An improved Huffman coding method for archiving text, images, and music characters in DNA. Biotechniques 47, 747-754 (2009).
Tsaftaris, S. A. & Katsaggelos, A. K. On designing DNA databases for the storage and retrieval of digital signals. Lecture Notes Comp. Sci. 3611, 1192-1201 (2005).
Nick Goldman et al: "Towards practical, high-capacity, low-maintenance information storage in synthesized DNA," Nature, Jan. 1, 2013 (Jan. 1, 2013.
G. M. Church et al: "Next-Generation Digital Information Storage in DNA," Science, vol. 337, No. 6102, Sep. 28, 2012 (Sep. 28, 2012), pp. 1628-1628.
Thomas P. Niedringhaus et al: "Landscape of Next-Generation Sequencing Technologies," Analytical Chemistry, vol. 83, No. 12, Jun. 15, 2011 (Jun. 15, 2011), pp. 4327-4341.
Sotiriosa Tsaftaris et al: "On Designing DNA Databases for the Storage and Retrieval of Digital Signals," Jul. 23, 2005 (Jul. 23, 2005), Advances in Natural Computation; [Lecture Notes in Computer Science;;LNCS], Springer-Verlag, Berlin/Heidelberg, pp. 1192-1201.

* cited by examiner

*Primary Examiner* — John S Brusca
(74) *Attorney, Agent, or Firm* — 24IP Law Group USA, PLLC; Timothy R DeWitt

(57) ABSTRACT

A method for storage of an item of information (210) is disclosed. The method comprises encoding bytes (720) in the item of information (210), and representing using a schema the encoded bytes by a DNA nucleotide to produce a DNA sequence (230). The DNA sequence (230) is broken into a plurality of overlapping DNA segments (240) and indexing information (250) added to the plurality of DNA segments. Finally, the plurality of DNA segments (240) is synthesized (790) and stored (795).

9 Claims, 7 Drawing Sheets

Specification includes a Sequence Listing.

5'-...GAGCATCTGCAGATGCTCATGAGCATCTGCAGATGCTCATGAGCATCTGCAGATGCTCAT...-3'
   |||||||||||||||||||||||||||||||||||||||||||||||||||||||||||
3'-...CTCGTAGACGTCTACGAGTACTCGTAGACGTCTACGAGTACTCGTAGACGTCTACGAG...-5'

SEQUENCE LISTING

<160> NUMBER OF SEQ ID NOS: 5

<210> SEQ ID NO 1
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
acactctttc cctacacgac gctcttccga tct                                    33

<210> SEQ ID NO 2
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
agatcggaag agcggttcag caggaatgcc gag                                    33

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
gagcatctgc agatgctcat                                                   20

<210> SEQ ID NO 4
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
tagatgtgta cagactacgc gcagcgagat cgactcgcag tgctgagtga cagactagtc       60
acgtcgcagc gctag                                                        75

<210> SEQ ID NO 5
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
gagcatctgc agatgctcat gagcatctgc agatgctcat gagcatctgc agatgctcat       60

HIGH-CAPACITY STORAGE OF DIGITAL INFORMATION IN DNA

CROSS-REFERENCE TO RELATED APPLICATIONS

The present application is a continuation of PCT Application No. PCT/EP2013/061300 filed on May 31, 2013, which claims the benefit of the filing date of U.S. Provisional Patent Application Ser. No. 61/654,295, filed on Jun. 1, 2012. The above-referenced applications are hereby incorporated by reference.

SEQUENCE LISTING

The instant application contains a Sequence Listing which has been submitted electronically in ASCII format and is hereby incorporated by reference in its entirety. Said ASCII copy, created on Jun. 1, 2015, is named 4091.91216USC1_SL.txt and is 1,592 bytes in size.

BACKGROUND OF THE INVENTION

Field of the Invention

The disclosure relates to a method and apparatus for the storage of digital information in DNA.

Brief Description of the Related Art

DNA has the capacity to hold vast amounts of information, readily stored for long periods in a compact form. Bancroft, C., Bowler, T., Bloom, B. & Clelland, C. T. Long-term storage of information in DNA. *Science* 293, 1763-1765 (2001) and Cox, J. P. L. Long-term data storage in DNA. *TRENDS Biotech.* 19, 247-250 (2001). The idea of using DNA as a store for digital information has existed since 1995. Baum, E. B. Building an associative memory vastly larger than the brain. *Science* 268, 583-585 (1995). Physical implementations of DNA storage have to date stored only trivial amounts of information—typically a few numbers or words of English text. Clelland, C. T., Risca, V. & Bancroft, C. Hiding messages in DNA microdots. *Nature* 399, 533-534 (1999); Kac, E. Genesis (1999) http://www.ekac.org/geninfo.html accessed online, 2 Apr. 2012; Wong, P. C., Wong, K.-K. & Foote, H. Organic data memory. Using the DNA approach. *Comm. ACM* 46, 95-98 (2003); Ailenberg, M. & Rotstein, O. D. An improved Huffman coding method for archiving text, images, and music characters in DNA. *Biotechniques* 47, 747-754 (2009); Gibson, D. G. et al. Creation of a bacterial cell controlled by a chemically synthesized genome. *Science* 329, 52-56 (2010). The inventors are unaware of large-scale storage and recovery of arbitrarily sized digital information encoded in physical DNA, rather than data storage on magnetic substrates or optical substrates.

Currently the synthesis of DNA is a specialized technology focused on biomedical applications. The cost of the DNA synthesis has been steadily decreasing over the past decade. It is interesting to speculate at what timescale data storage in a DNA molecule, as disclosed herein, would be more cost effective than the current long term archiving process of data storage on tape with rare but regular transfer to new media every 3 to 5 years. Current "off the shelf" technology for DNA synthesis equates to a price of around 100 bytes per U.S. dollar. Newer technology commercially available from Agilent Technologies (Santa Clara, Calif.) may substantially decrease this cost. However, account also needs to be made for regular transfer of data between tape media. The questions are both the costs for this transfer of data and whether this cost is fixed or diminishes over time. If a substantial amount of the cost is assumed to be fixed, then there is a time horizon at which use of DNA molecules for data storage is more cost effective than regular data storage on the tape media. After 400 years (at least 80 media transfers), it is possible that this data storage using DNA molecules is already cost effective.

The high capacity of DNA to store information stably under easily achieved conditions has made DNA an attractive target for information storage since 1995. In addition to information density, DNA molecules have a proven track record as an information carrier, longevity of the DNA molecule is known and the fact that, as a basis of life on Earth, methods for manipulating, storing and reading the DNA molecule will remain the subject of continual technological innovation while there remains DNA-based intelligent life. Data storage systems based on both living vector DNA (in vivo DNA molecules) and on synthesized DNA (in vitro DNA) have been proposed. The in vivo data storage systems have several disadvantages. Such disadvantages include constraints on the quantity, genomic elements and locations that can be manipulated without affecting viability of the DNA molecules in the living vector organisms. Examples of such living vector organisms include but are not limited to bacteria. The reduction in viability includes decreasing capacity and increasing the complexity of information encoding schemes. Furthermore, germline and somatic mutation will cause fidelity of the stored information and decoded information to be reduced over time and possibly a requirement for storage conditions of the living DNA to be carefully regulated.

In contrast, the "isolated DNA" (i.e., in vitro DNA) is more easily "written" and routine recovery of examples of the non-living DNA from samples that are tens of thousands of years old indicates that a well-prepared non-living DNA sample should have an exceptionally long lifespan in easily-achieved low-maintenance environments (i.e. cold, dry and dark environments). See, Shapiro, B. et al. Rise and fall of the Beringian steppe bison. *Science* 306, 1561-1565 (2004); Poinar, H. K. et al. Metagenomics to paleogenomics: large-scale sequencing of mammoth DNA. *Science* 311, 392-394 (2005); Willerslev, E. et al. Ancient biomolecules from deep ice cores reveal a forested southern Greenland. *Science* 317, 111-114 (2007); Green, R. E. et al. A draft sequence of the Neanderthal genome. *Science* 328, 710-722 (2010); Anchordoquy, T. J. & Molina, M. C. Preservation of DNA. *Cell Preservation Tech.* 5, 180-188 (2007); Bonnet, J. et al. Chain and conformation stability of solid-state DNA: implications for room temperature storage. *Nucl. Acids Res.* 38, 1531-1546 (2010); Lee, S. B., Crouse, C. A. & Kline, M. C. Optimizing storage and handling of DNA extracts. *Forensic Sci. Rev.* 22, 131-144 (2010).

Previous work on the storage of information (also termed data) in the DNA has typically focused on "writing" a human-readable message into the DNA in encoded form, and then "reading" the encoded human-readable message by determining the sequence of the DNA and decoding the sequence. Work in the field of DNA computing has given rise to schemes that in principle permit large-scale associative (content-addressed) memory, but there have been no attempts to develop this work as practical DNA-storage schemes. Baum, E. B. Building an associative memory vastly larger than the brain. *Science* 268, 583-585 (1995); Tsaftaris, S. A. & Katsaggelos, A. K. On designing DNA databases for the storage and retrieval of digital signals. *Lecture Notes Comp. Sci.* 3611, 1192-1201 (2005); Yamamoto, M., Kashiwamura, S., Ohuchi, A. & Furukawa, M.

Large-scale DNA memory based on the nested PCR. *Natural Computing* 7, 335-346 (2008); Kari, L. & Mahalingam, K. DNA computing: a research snapshot. In Atallah, M. J. & Blanton, M. (eds.) *Algorithms and Theory of Computation Handbook*, vol. 2. 2nd ed. pp. 31-1-31-24 (Chapman & Hall, 2009). FIG. 1 shows the amounts of information successfully encoded and recovered in 14 previous studies (note the logarithmic scale on the y-axis). Points are shown for 14 previous experiments (open circles) and for the present disclosure (solid circle). The largest amount of human-readable messages stored this way is 1280 characters of English language text[8], equivalent to approximately 6500 bits of Shannon information. Gibson, D. G. et al. Creation of a bacterial cell controlled by a chemically synthesized genome. *Science* 329, 52-56 (2010); MacKay, D. J. C. *Information Theory, Inference, and Learning Algorithms*. (Cambridge University Press, 2003).

The Indian Council of Scientific and Industrial Research has filed a U.S. Patent Application Publication No. 2005/0053968 (Bharadwaj et al) that teaches a method for storing information in DNA. The method of U.S. '968 comprises using an encoding method that uses 4-DNA bases representing each character of an extended ASCII character set. A synthetic DNA molecule is then produced, which includes the digital information, an encryption key, and is flanked on each side by a primer sequence. Finally, the synthesized DNA is incorporated in a storage DNA. In the event that the amount of DNA is too large, then the information can be fragmented into a number of segments. The method disclosed in U.S. '968 is able to reconstruct the fragmented DNA segments by matching up the header primer of one of the segments with the tail primer on the subsequent one of the segments.

Other patent publications are known which describe techniques for storing information in DNA. For example, U.S. Pat. No. 6,312,911 teaches a steganographic method for concealing coded messages in DNA. The method comprises concealing a DNA encoded message within a genomic DNA sample followed by further concealment of the DNA sample to a microdot. The application of this U.S. '911 patent is in particular for the concealment of confidential information. Such information is generally of limited length and thus the document does not discuss how to store items of information that are of longer length. The same inventors have filed an International Patent Application published as International Publication No. WO 03/025123.

SUMMARY OF THE INVENTION

A practical encoding-decoding procedure that stores more information than previously handled is described in this disclosure. The inventors have encoded five computer files—totaling 757051 bytes (739 kB) of hard disk storage and with an estimated Shannon information of $5.2 \times 10^6$ bits—into a DNA code. The inventors subsequently synthesized this DNA, transported the synthesized DNA from the USA to Germany via the UK, sequenced the DNA and reconstructed all five computer files with 100% accuracy.

The five computer files included an English language text (all 154 of Shakespeare's sonnets), a PDF document of a classic scientific paper, a JPEG colour photograph and an MP3 format audio file containing 26 seconds of speech (from Martin Luther King's "I Have A Dream" speech). Watson, J. D. & Crick, F. H. C. Molecular structure of nucleic acids. *Nature* 171, 737-738 (1953). This data storage represents approximately 800 times as much information as the known previous DNA-based storage and covers a much greater variety of digital formats. The results demonstrate that DNA storage is increasingly realistic and could, in future, provide a cost-effective means of archiving digital information and may already be cost effective for low access, multi-decade archiving tasks.

A method for storage of an item of information is disclosed. The method comprises encoding bytes in the item of information. The encoded bytes are represented using a schema by a DNA nucleotide to produce a DNA sequence in-silico. In a next step, the DNA sequence is split into a plurality of overlapping DNA segments and indexing information is added to the plurality of DNA segments. Finally, the plurality of DNA segments is synthesized and stored.

The addition of the indexing information to the DNA segments means that the position of the segments in the DNA sequence representing the item of information can be uniquely identified. There is no need to rely on a matching of a head primer with a tail primer. This makes it possible to recover almost the entire item of information, even if one of the segments has failed to reproduce correctly. If no indexing information were present, then there is a risk that it might not be possible to correctly reproduce the entire item of information if the segments could not be matched to each other due to "orphan" segments whose position in the DNA sequence cannot be clearly identified.

The use of overlapping DNA segments means that a degree of redundancy is built into the storage of the items of information. If one of the DNA segments cannot be decoded, then the encoded bytes can still be recovered from neighboring ones of the DNA segments. Redundancy is therefore built into the system.

Multiple copies of the DNA segments can be made using known DNA synthesis techniques. This provides an additional degree of redundancy to enable the item of information to be decoded, even if some of copies of the DNA segments are corrupted and cannot be decoded.

In one aspect of the invention, the representation schema used for encoding is designed such that adjacent ones of the DNA nucleotides are different. This is to increase the reliability of the synthesis, reproduction and sequencing (reading) of the DNA segments In a further aspect of the invention, a parity-check is added to the indexing information. This parity check enables erroneous synthesis, reproduction or sequencing of the DNA segments to be identified. The parity-check can be expanded to also include error correction information.

Alternate ones of the synthesized DNA segments are reverse complemented. These provide an additional degree of redundancy in the DNA and means that there is more information available if any of the DNA segment is corrupted.

DESCRIPTION OF THE FIGURES

For a more complete understanding of the present invention and the advantages thereof, reference is now made to the following description and the accompanying drawings, in which.

DETAILED DESCRIPTION

Figure 1:
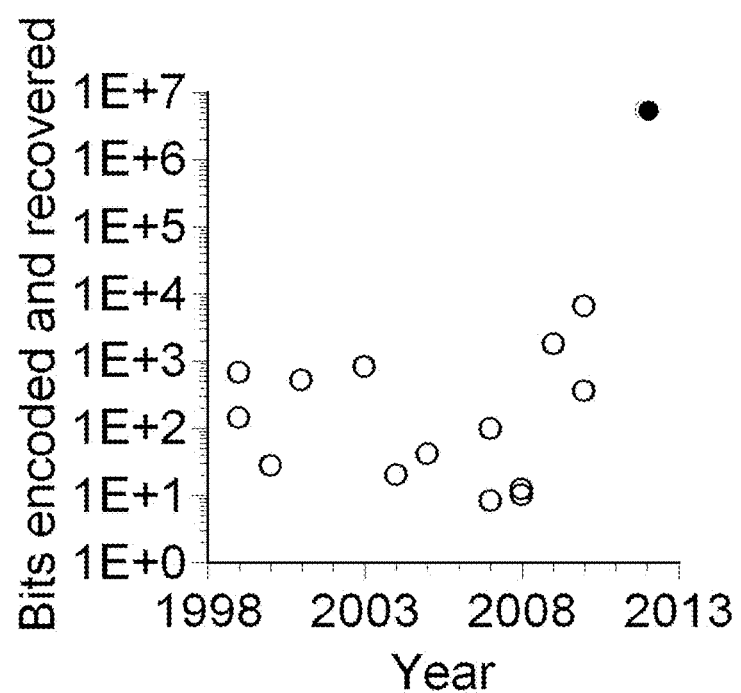
FIG. 1 is a graph of amounts of information stored in DNA and successfully recovered, as a function of time.

One of the main challenges for a practical implementation of DNA storage to date has been the difficulty of creating long sequences of DNA to a specified design. The long sequences of DNA are required to store large data files, such as long text items and videos. It is also preferable to use an encoding with a plurality of copies of each designed DNA. Such redundancy guards against both encoding and decoding errors, as will be explained below. It is not cost-efficient to use a system based on individual long DNA chains to encode each (potentially large) message. The inventors have developed a method that uses 'indexing' information associated with each one of the DNA segments to indicate the position of the DNA segment in a hypothetical longer DNA molecule that encodes the entire message.

The inventors used methods from code theory to enhance the recoverability of the encoded messages from the DNA segment, including forbidding DNA homopolymers (i.e. runs of more than one identical base) that are known to be associated with higher error rates in existing high throughput technologies. The inventors further incorporated a simple error-detecting component, analogous to a parity-check bit[9] into the indexing information in the code. More complex schemes, including but not limited to error-correcting codes and, indeed, substantially any form of digital data security (e.g. RAID-based schemes) currently employed in informatics, could be implemented in future developments of the DNA storage scheme. See, Baum, E. B. Building an associative memory vastly larger than the brain. *Science* 268, 583-585 (1995) and Chen, P. M., Lee, E. K., Gibson, G. A., Katz, R. H. & Patterson, D. A. RAID: high-performance, reliable secondary storage. *ACM Computing Surveys* 26, 145-185 (1994).

The inventors selected five computer files to be encoded as a proof-of-concept for the DNA storage of this disclosure. Rather than restricting the files to human-readable information, files using a range of common formats were chosen. This demonstrated the ability of the teachings of the disclosure to store arbitrary types of digital information. The files contained all 154 of Shakespeare's sonnets (in TXT format), the complete text and figure of ref 10 (in PDF format), a medium-resolution color photograph of the EMBL-European Bioinformatics Institute (JPEG 2000 format), a 26 second extract from Martin Luther King's "I Have A Dream" speech (MP3 format) and a file defining the Huffman code used in this study to convert bytes to base-3 digits (as a human-readable text file).

The five files selected for DNA-storage were as follows.

wssnt10.txt—107738 bytes—ASCII text format all 154 Shakespeare sonnets (from Project Gutenberg, http://www.gutenberg.org/ebooks/1041)

watsoncrick.pdf—280864 bytes—PDF format document Watson and Crick's (1953) publication[10] describing the structure of DNA (from the *Nature* website, http://www.nature.com/nature/dna50/archive.html, modified to achieve higher compression and thus smaller file size).

EBI.jp2—184264 bytes—JPEG 2000 format image file color photograph (16.7M colors, 640×480 pixel resolution) of the EMBL-European Bioinformatics Institute (own picture).

MLK_excerpt_VBR_45-85.mp3—168539 bytes—MP3 format sound file 26 second-long extract from Martin Luther King's "I Have A Dream" speech (from http://www.americanrhetoric.com/speeches/mlkihaveadream.htm, modified to achieve higher compression: variable bit rate, typically 48-56 kbps; sampling frequency 44.1 kHz)

View_huff3.cd.new—15646 bytes—ASCII file human-readable file defining the Huffman code used in this study to convert bytes to base-3 digits (trits)

The five computer files comprise a total of 757051 bytes, approximately equivalent to a Shannon information of $5.2 \times 10^6$ bits or 800 times as much encoded and recovered human-designed information as the previous maximum amount known to have been stored (see FIG. 1).

Figure 7:
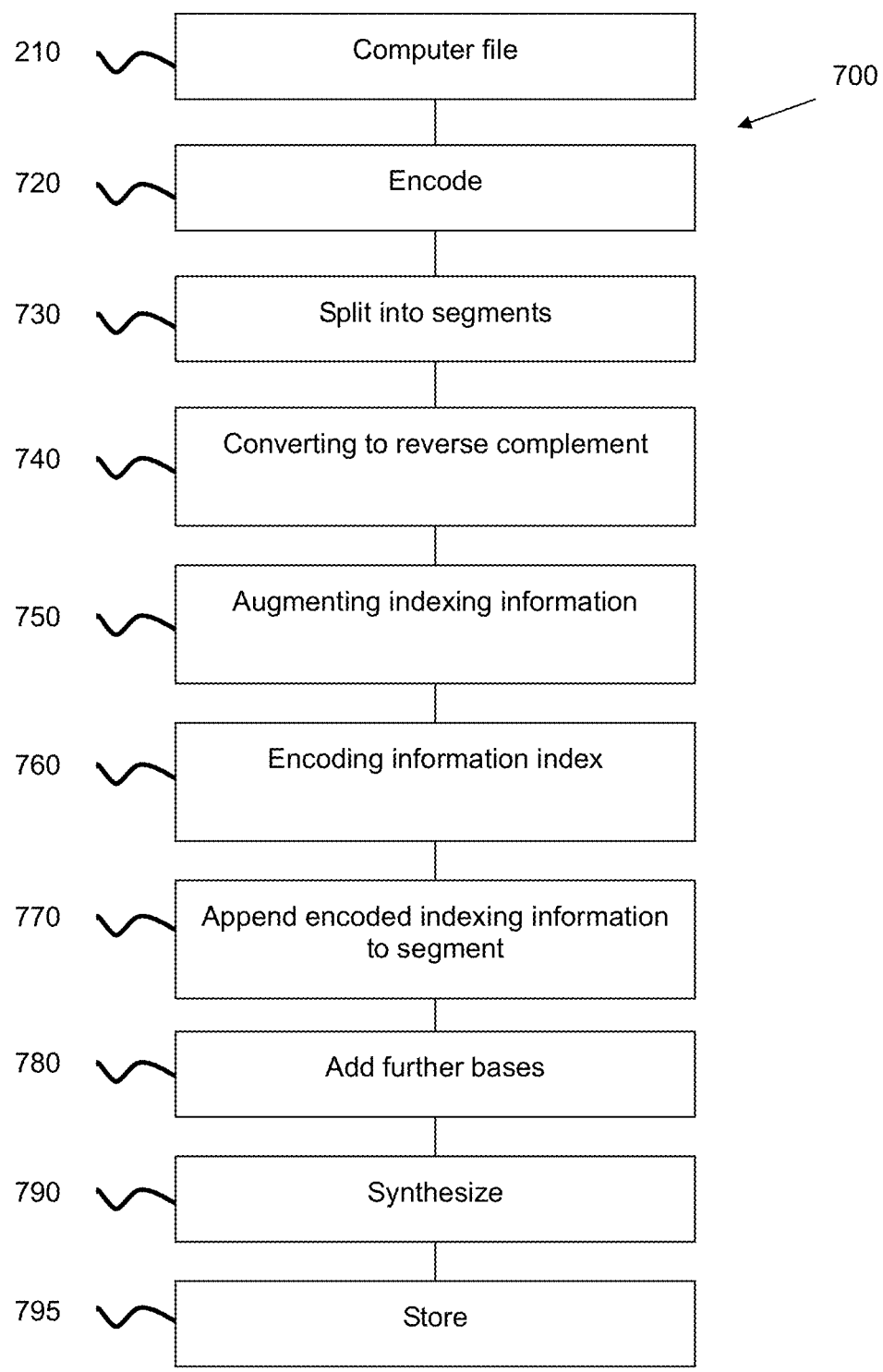
FIG. 7 shows a flow diagram of the encoding of the method.

The DNA encoding of each one of the computer files was computed using software and the method is illustrated in FIG. 7. In one aspect of the invention 700 described herein, the bytes comprising each computer file 210 were represented in step 720 as a DNA sequence 230 with no homopolymers by an encoding scheme to produce an encoded file 220 that replaces each byte by five or six bases (see below) forming the DNA sequence 230. The code used in the encoding scheme was constructed to permit a straightforward encoding that is close to the optimum information capacity for a run length-limited channel (i.e., no repeated nucleotides). It will, however, be appreciated that other encoding schemes may be used.

The resulting in silico DNA sequences 230 are too long to be readily produced by standard oligonucleotide synthesis. Each of the DNA sequences 230 was therefore split in step 730 into overlapping segments 240 of length 100 bases with an overlap of 75 bases. To reduce the risk of systematic synthesis errors introduced to any particular run of bases, alternate ones of the segments were then converted in step 740 to their reverse complement, meaning that each base is "written" four times, twice in each direction. Each segment was then augmented in step 750 with an indexing information 250 that permitted determination of the computer file from which the segment 240 originated and its location within that computer file 210, plus simple error-detection information. This indexing information 250 was also encoded in step 760 as non-repeating DNA nucleotides, and appended in step 770 to the 100 information storage bases of the DNA segments 240. It will be appreciated that the division of the DNA segments 240 into lengths of 100 bases with an overlap of 75 bases is purely arbitrary. It would be possible for other lengths and overlaps to be used and this is not limiting of the invention.

In total, all of the five computer files were represented by 153335 strings of DNA. Each one of the strings of DNA comprised 117 nucleotides (encoding original digital information plus indexing information). The encoding scheme used had various features of the synthesized DNA (e.g. uniform segment lengths, absence of homopolymers) that made it obvious that the synthesized DNA did not have a natural (biological) origin. It is therefore obvious that the synthesized DNA has a deliberate design and encoded information. See, Cox, J. P. L. Long-term data storage in DNA. *TRENDS Biotech.* 19, 247-250 (2001).

As noted above, other encoding schemes for the DNA segments 240 could be used, for example to provide enhanced error-correcting properties. It would also be straightforward to increase the amount of indexing information in order to allow more or larger files to be encoded. It has been suggested that the Nested Primer Molecular Memory (NPMM) scheme reaches its practical maximum capacity at 16.8M unique addresses, and there appears to be no reason why the method of the disclosure could not be extended beyond this to enable the encoding of almost arbitrarily large amounts of information. See, Yamamoto, M., Kashiwamura, S., Ohuchi, A. & Furukawa, M. Large-scale DNA memory based on the nested PCR. *Natural Computing* 7, 335-346 (2008) and Kari, L. & Mahalingam, K. DNA computing: a research snapshot. In Atallah, M. J. & Blanton, M. (eds.) *Algorithms and Theory of Computation Handbook*, vol. 2. 2nd ed. pp. 31-1-31-24 (Chapman & Hall, 2009)

One extension to the coding scheme in order to avoid systematic patterns in the DNA segments 240 would be to add change the information. Two ways of doing this were tried. A first way involved the "shuffling" of information in the DNA segments 240, the information can be retrieved if one knows the pattern of shuffling. In one aspect of the disclosure different patterns of shuffles were used for different ones of the DNA segments 240.

A further way is to add a degree of randomness into the information in each one of the DNA segments 240. A series of random digits can be used for this, using modular addition of the series of random digits and the digits comprising the information encoded in the DNA segments 240. The information can easily be retrieved by modular subtraction during decoding if one knows the series of random digits used. In one aspect of the disclosure, different series of random digits were used for different ones of the DNA segments 240.

Figure 2:
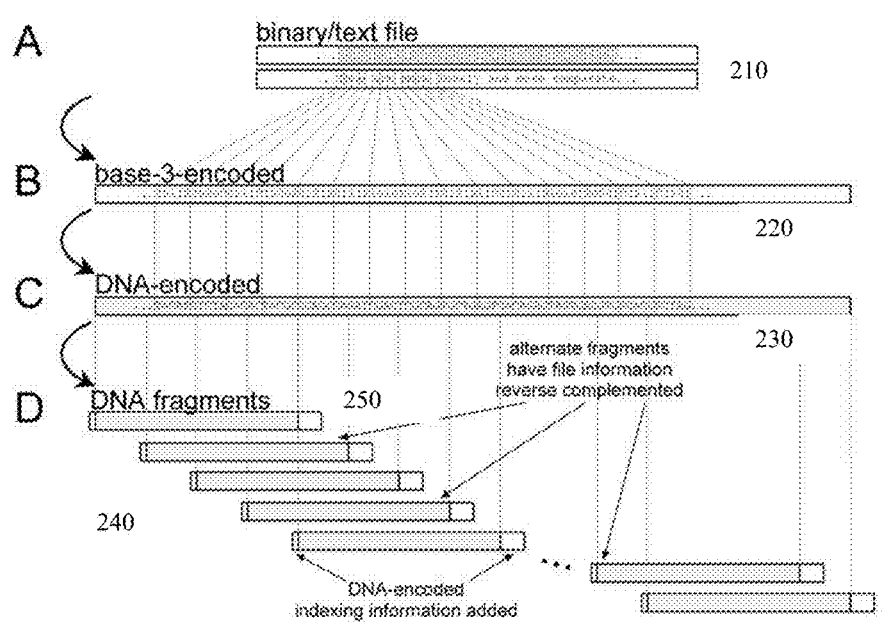
FIG. 2 shows an example of the method of the present disclosure. Figure discloses SEQ ID NO: 4.

The digital information encoding in step 720 was carried out as follows. The five computer files 210 of digital information (represented in FIG. 2A) stored on a hard-disk drive were encoded using software. Each byte of each one of the five computer files 210 to be encoded in step 720 was represented as a sequence of DNA bases via base-3 digits ('trits' 0, 1 and 2) using a purpose-designed Huffman code listed in Table 1 (below) to produce the encoded file 220. This exemplary coding scheme is shown in outline in FIG. 2B. Each of the 256 possible bytes was represented by five or six trits. Subsequently, each one of the trits was encoded as a DNA nucleotide 230 selected from the three nucleotides different from the previous nucleotide (FIG. 2C). In other words, in the encoding scheme chosen for this aspect of the disclosure, each one of the three nucleotides was different from the previous one used to ensure no homopolymers. The resulting DNA sequence 230 was split in step 730 to DNA segments 240 of length 100 bases, as shown in FIG. 2D. Each one of the DNA segments overlapped the previous DNA segment by 75 bases, to give DNA segments of a length that was readily synthesized and to provide redundancy. Alternate ones of the DNA segments were reverse complemented.

The indexing information 250 comprised two trits for file identification (permitting $3^2$=9 files to be distinguished, in this implementation), 12 trits for intra-file location information (permitting $3^{12}$=531441 locations per file) and one 'parity-check' trit. The indexing information 250 was encoded in step 760 as non-repeating DNA nucleotides and was appended in step 770 to the 100 information storage bases. Each indexed DNA segment 240 had one further base added in step 780 at each end, consistent with the 'no homopolymers' rule, that would indicate whether the entire DNA segment 240 were reverse complemented during the 'reading' stage of the experiment.

In total, the five computer files 210 were represented by 153335 strings of DNA, each comprising 117 (1+100+2+12+1+1) nucleotides (encoding original digital information and indexing information).

The data-encoding component of each string in the aspect of the invention described herein can contain Shannon information at 5.07 bits per DNA base, which is close to the theoretical optimum of 5.05 bits per DNA base for base-4 channels with run length limited to one. The indexing implementation 250 permits $3^{14}$=4782969 unique data locations. Increasing the number of indexing trits (and therefore bases) used to specify file and intra-file location by just two, to 16, gives $3^{16}$=43046721 unique locations, in excess of the 16.8M that is the practical maximum for the NPMM scheme. See, Yamamoto, M., Kashiwamura, S., Ohuchi, A. & Furukawa, M. Large-scale DNA memory based on the nested PCR. *Natural Computing* 7, 335-346 (2008) and Kari, L. & Mahalingam, K. DNA computing: a research snapshot. In Atallah, M. J. & Blanton, M. (eds.) *Algorithms and Theory of Computation Handbook*, vol. 2. 2nd ed. pp. 31-1-31-24 (Chapman & Hall, 2009)

The DNA synthesis process of step 790 was also used to incorporate 33 bp adapters to each end of each one of the oligonucleotides (oligo) to facilitate sequencing on Illumina sequencing platforms:

```
5' adapter:
                                    (SEQ ID NO: 1)
ACACTCTTTCCCTACACGACGCTCTTCCGATCT 3' adapter:
                                    (SEQ ID NO: 2)
AGATCGGAAGAGCGGTTCAGCAGGAATGCCGAG
```

The 153335 DNA segment designs 240 were synthesized in step 790 in three distinct runs (with the DNA segments 240 randomly assigned to runs) using an updated version of Agilent Technologies' OLS (Oligo Library Synthesis) process described previously[22,23] to create approx. $1.2 \times 10^7$ copies of each DNA segment design. Errors were seen to occur in only about one error per 500 bases and independently in different copies of the DNA segments 240. Agilent Technologies adapted the phosphoramidite chemistry developed previously[24] and employed inkjet printing and flow cell reactor technologies in Agilent's SurePrint in situ microarray synthesis platform. The inkjet printing within an anhydrous chamber allows the delivery of very small volumes of phosphoramidites to a confined coupling area on a 2D planar surface, resulting in the addition of hundreds of thousands of bases in parallel. Subsequent oxidation and detritylation are carried out in a flow cell reactor. Once the DNA synthesis has been completed, the oligonucleotides are then cleaved from the surface and deprotected. See, Cleary, M. A. et al. Production of complex nucleic acid libraries using highly parallel in situ oligonucleotide synthesis. *Nature Methods* 1, 241-248 (2004).

The adapters were added to the DNA segments to enable a plurality of copies of the DNA segments to be easily made. A DNA segment with no adapter would require additional chemical processes to "kick start" the chemistry for the synthesis of the multiple copies by adding additional groups onto the ends of the DNA segments.

Up to ~99.8% coupling efficiency is achieved by using thousands-fold excess of phosphoramidite and activator solution. Similarly, millions-fold excess of detritylation agent drives the removal of the 5'-hydroxyl protecting group to near completion. A controlled process in the flowcell reactor significantly reduced depurination, which is the most prevalent side reaction. See, Le Proust, E. M. et al. Synthesis of high-quality libraries of long (150 mer) oligonucleotides by a novel depurination controlled process. *Nucl. Acids Res.*

38, 2522-2540 (2010). Up to 244000 unique sequences can be synthesized in parallel and delivered as ~1-10 picomole pools of oligos.

Figure 8:
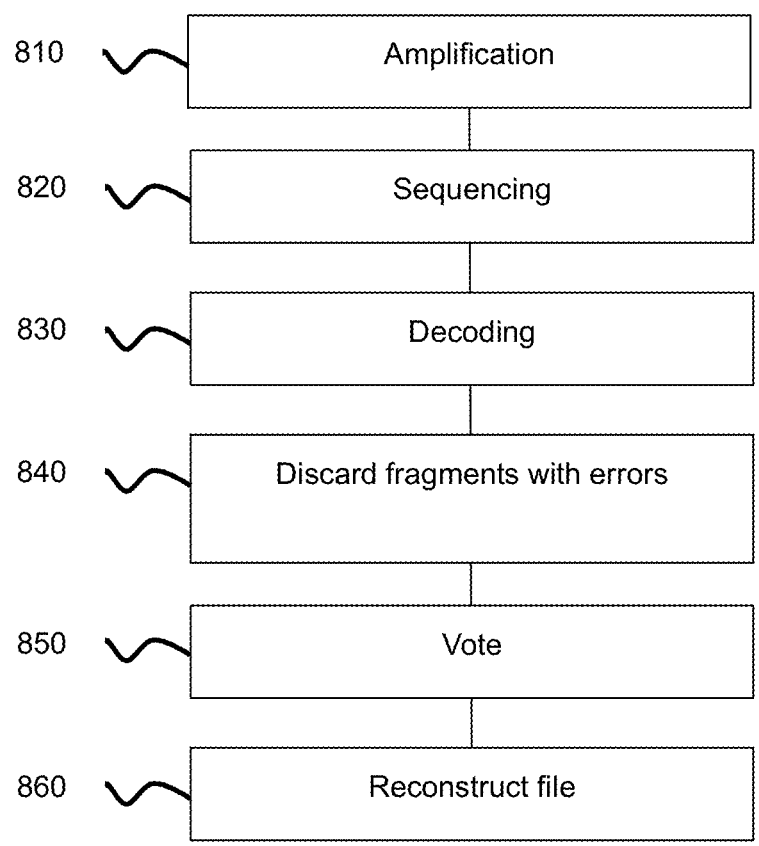
FIG. 8 shows a flow diagram of the decoding of the method.

The three samples of lyophilized oligos were incubated in Tris buffer overnight at 4° C., periodically mixed by pipette and vortexing, and finally incubated at 50° C. for 1 hour, to a concentration of 5 ng/ml. As insolubilized material remained, the samples were left for a further 5 days at 4° C. with mixing two-four times each day. The samples were then incubated at 50° C. for 1 hour and 68° C. for 10 minutes, and purified from residual synthesis byproducts on Ampure XP paramagnetic beads (Beckman Coulter) and could be stored in step 795. Sequencing and decoding is shown in FIG. 8.

The combined oligo sample was amplified in step 810 (22 PCR cycles using thermocycler conditions designed to give even A/T vs. G/C processing[26]) using paired-end Illumina PCR primers and high-fidelity AccuPrime reagents (Invitrogen), a combination of Taq and Pyrococcus polymerases with a thermostable accessory protein. The amplified products were bead purified and quantified on an Agilent 2100 Bioanalyzer, and sequenced using AYB software in paired-end mode on an Illumina HiSeq 2000 to produce reads of 104 bases.

The digital information decoding was carried out as follows. The central 91 bases of each oligo were sequenced in step 820 from both ends and so rapid computation of full-length (117 base) oligos and removal of sequence reads inconsistent with the designs was straightforward. The sequence reads were decoded in step 830 using computer software that exactly reverses the encoding process. The sequence reads for which the parity-check trit indicated an error or that at any stage could not be unambiguously decoded or assigned to a reconstructed computer file were discarded in step 840 from further consideration.

The vast majority of locations within every decoded file were detected in multiple different sequenced DNA oligos, and simple majority voting in step 850 was used to resolve any discrepancies caused by the DNA synthesis or the sequencing errors. On completion of this procedure 860, four of the five original computer files 210 were reconstructed perfectly. The fifth computer file required manual intervention to correct two regions each of 25 bases that were not recovered from any sequenced read.

During decoding in step 850, it was noticed that one file (ultimately determined to be watsoncrick.pdf) reconstructed in silico at the level of DNA (prior to decoding, via base-3, to bytes) contained two regions of 25 bases that were not recovered from any one of the sequenced oligos. Given the overlapping segment structure of the encoding, each region indicated the failure of four consecutive segments to be synthesized or sequenced, as any one of four consecutive overlapping segments would have contained bases corresponding to this location. Inspection of the two regions indicated that the non-detected bases fell within long repeats of the following 20-base motif:

(SEQ ID NO: 3)
5' GAGCATCTGCAGATGCTCAT 3'

Figures 4, 5:
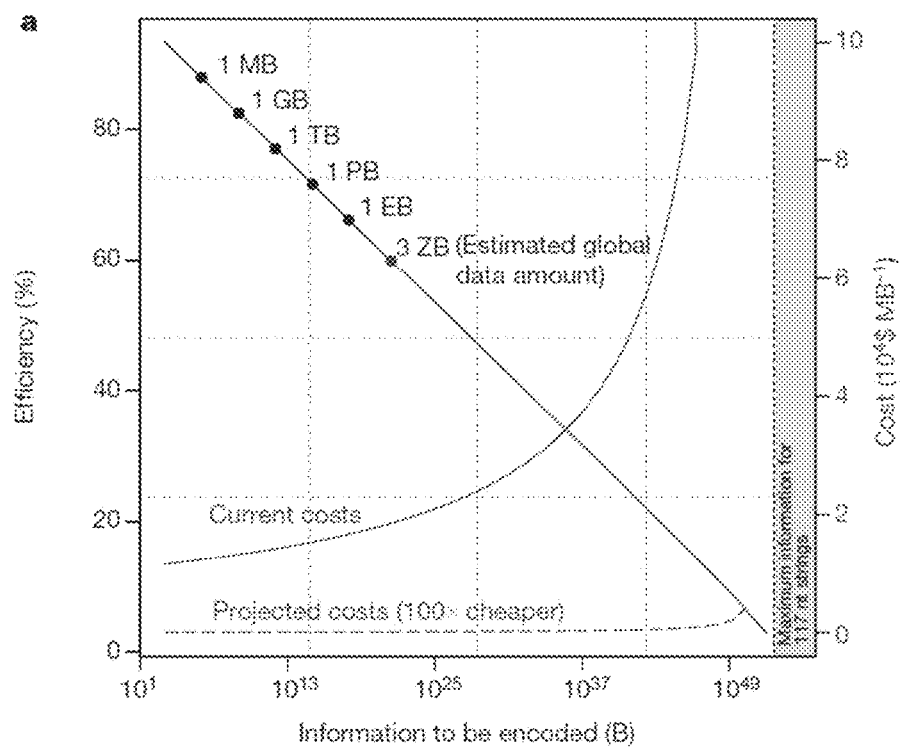
FIG. 4 shows a motif with a self-reverse complementary pattern (SEQ ID NO: 5).
FIG. 5 shows the encoding efficiency.

It was noticed that repeats of this motif have a self-reverse complementary pattern. These are shown in FIG. 4.

It is possible that long, self-reverse complementary DNA segments might not be readily sequenced using the Illumina paired-end process, owing to the possibility that the DNA segments might form internal nonlinear stem-loop structures that would inhibit the sequencing-by-synthesis reaction used in the protocol used in the method described in this document. Consequently, the in silico DNA sequence was modified to repair the repeating motif pattern and then subjected to subsequent decoding steps. No further problems were encountered, and the final decoded file matched perfectly the file watsoncrick.pdf. A code that ensured that no long self-complementary regions existed in any of the designed DNA segments could be used in future.

Example of Huffman Coding Scheme

Table 1 shows an example of the exemplary Huffman coding scheme used to convert byte values (0-255) to base-3. For highly compressed information, each byte value should appear equally frequently and the mean number of trits per byte will be (239*5+17*6)/256=5.07. The theoretical maximum number of trits per byte is log(256)/log(3)=5.05.

TABLE 1

| Code Word No | 8-bit ASCII Character | Byte Value | Base 3 Coding (5 or 6 trits) |
|---|---|---|---|
| 0 |  | 0 | 22201 |
| 1 | U | 85 | 22200 |
| 2 | ™ | 170 | 22122 |
| 3 |  | 127 | 22121 |
| 4 | " | 253 | 22120 |
| 5 | 4 | 52 | 22112 |
| 6 | ä | 138 | 22111 |
| 7 | ) | 41 | 22110 |
| 8 | V | 86 | 22102 |
| 9 | * | 42 | 22101 |
| 10 | d | 100 | 22100 |
| 11 | , | 44 | 22022 |
| 12 |  | 250 | 22020 |
| 13 | Ñ | 132 | 22021 |
| 14 | ° | 161 | 22012 |
| 15 | b | 98 | 22010 |
| 16 |  | 8 | 22002 |
| 17 | " | 34 | 22011 |
| 18 | [NL] | 10 | 22001 |
| 19 | ï | 149 | 22000 |
| 20 | W | 87 | 21222 |
| 21 |  | 21 | 21221 |
| 22 | J | 74 | 21220 |
| 23 | $ | 36 | 21212 |
| 24 | E | 69 | 21210 |
| 25 | ± | 177 | 21202 |
| 26 |  | 20 | 21211 |
| 27 | ' | 213 | 21200 |
| 28 | £ | 163 | 21201 |
| 29 | Â | 229 | 21121 |
| 30 | ˇ | 255 | 21122 |
| 31 | ≈ | 197 | 21120 |
| 32 | Ö | 133 | 21112 |
| 33 | , | 252 | 21110 |
| 34 |  | 26 | 21111 |
| 35 | ≠ | 173 | 21101 |
| 36 | ó | 151 | 21102 |
| 37 | R | 82 | 21100 |
| 38 | K | 75 | 21022 |
| 39 | % | 37 | 21021 |
| 40 | ¶ | 166 | 21011 |
| 41 | ø | 191 | 21020 |
| 42 | X | 88 | 21012 |
| 43 | ? | 63 | 21010 |
| 44 | D | 68 | 21001 |
| 45 | ñ | 150 | 21002 |
| 46 | L | 76 | 21000 |
| 47 |  | 4 | 20222 |
| 48 | ö | 154 | 20221 |
| 49 | í | 234 | 20212 |
| 50 |  | 22 | 20220 |
| 51 | ¢ | 162 | 20211 |
| 52 | i | 105 | 20210 |
| 53 | f | 102 | 20202 |
| 54 | ' | 171 | 20201 |
| 55 | h | 104 | 20200 |

TABLE 1-continued

| Code Word No | 8-bit ASCII Character | Byte Value | Base 3 Coding (5 or 6 trits) |
|---|---|---|---|
| 56 | © | 169 | 20122 |
| 57 | f | 196 | 20121 |
| 58 | – | 208 | 20120 |
| 59 | T | 84 | 20112 |
| 60 | Ç | 130 | 20111 |
| 61 | í | 146 | 20102 |
| 62 | H | 72 | 20110 |
| 63 |  | 16 | 20101 |
| 64 | B | 66 | 20100 |
| 65 |  | 24 | 20022 |
| 66 | j | 106 | 20012 |
| 67 | fl | 223 | 20020 |
| 68 | : | 58 | 20021 |
| 69 | â | 137 | 20011 |
| 70 | I | 73 | 20010 |
| 71 | e | 101 | 20001 |
| 72 | ® | 168 | 20002 |
| 73 | µ | 181 | 12221 |
| 74 | Ø | 175 | 12222 |
| 75 | ° | 251 | 20000 |
| 76 | ( | 40 | 12220 |
| 77 | å | 140 | 12212 |
| 78 |  | 17 | 12211 |
| 79 | S | 83 | 12210 |
| 80 | ' | 254 | 12202 |
| 81 |  | 240 | 12201 |
| 82 | ÷ | 214 | 12200 |
| 83 | 5 | 53 | 12122 |
| 84 |  | 202 | 12112 |
| 85 |  | 25 | 12121 |
| 86 |  | 18 | 12120 |
| 87 | ˜ | 247 | 12111 |
| 88 | Æ | 174 | 12110 |
| 89 | p | 112 | 12102 |
| 90 | Y | 89 | 12101 |
| 91 | " | 210 | 12100 |
| 92 | Ÿ | 217 | 12012 |
| 93 | ¯ | 248 | 12020 |
| 94 | ¬ | 194 | 12021 |
| 95 | ə | 182 | 12022 |
| 96 | P | 80 | 12011 |
| 97 | O | 79 | 12002 |
| 98 | √ | 195 | 12010 |
| 99 |  | 12 | 12001 |
| 100 | — | 209 | 12000 |
| 101 | • | 165 | 11222 |
| 102 | ¹ | 245 | 11221 |
| 103 |  | 2 | 11220 |
| 104 | Q | 81 | 11212 |
| 105 | & | 38 | 11211 |
| 106 | ç | 141 | 11202 |
| 107 | " | 211 | 11210 |
| 108 | Ô | 239 | 11200 |
| 109 | - | 95 | 11201 |
| 110 | + | 43 | 11122 |
| 111 | ‡ | 224 | 11121 |
| 112 | Á | 203 | 11112 |
| 113 | ë | 145 | 11120 |
| 114 | ì | 147 | 11110 |
| 115 |  | 19 | 11111 |
| 116 | 2 | 50 | 11101 |
| 117 | à | 136 | 11102 |
| 118 | k | 107 | 11100 |
| 119 | Ü | 134 | 11022 |
| 120 | m | 109 | 11021 |
| 121 | ô | 153 | 11020 |
| 122 | î | 148 | 11002 |
| 123 | Ö | 205 | 11010 |
| 124 | ' | 212 | 11011 |
| 125 | 6 | 54 | 11012 |
| 126 | Ò | 241 | 11000 |
| 127 | ú | 156 | 11001 |
| 128 | s | 115 | 10222 |
| 129 | t | 116 | 10221 |
| 130 | N | 78 | 10220 |
| 131 | C | 67 | 10211 |
| 132 | F | 70 | 10212 |
| 133 | ≤ | 178 | 10210 |
| 134 | ü | 159 | 10202 |
| 135 | é | 142 | 10201 |
| 136 | \ | 92 | 10200 |
| 137 | 0 | 48 | 10122 |
| 138 | Z | 90 | 10120 |
| 139 | / | 218 | 10121 |
| 140 | ~ | 126 | 10112 |
| 141 | ' | 39 | 10111 |
| 142 | € | 219 | 10102 |
| 143 | ß | 167 | 10110 |
| 144 | r | 114 | 10101 |
| 145 | ¨ | 172 | 10022 |
| 146 |  | 14 | 10100 |
| 147 | x | 120 | 10020 |
| 148 | ã | 139 | 10021 |
| 149 | † | 160 | 10012 |
| 150 | ! | 33 | 10011 |
| 151 | ≥ | 179 | 10010 |
| 152 | u | 117 | 10002 |
| 153 | . | 225 | 10001 |
| 154 | Å | 129 | 10000 |
| 155 | Σ | 183 | 02222 |
| 156 | Ê | 230 | 02220 |
| 157 | # | 35 | 02221 |
| 158 | ] | 93 | 02210 |
| 159 |  | 6 | 02211 |
| 160 |  | 32 | 02212 |
| 161 | 8 | 56 | 02201 |
| 162 | û | 158 | 02202 |
| 163 | π | 185 | 02121 |
| 164 | / | 47 | 02122 |
| 165 | è | 143 | 02200 |
| 166 | { | 123 | 02111 |
| 167 | Â | 204 | 02120 |
| 168 | Û | 242 | 02112 |
| 169 | o | 111 | 02110 |
| 170 | g | 103 | 02102 |
| 171 | l | 108 | 02101 |
| 172 | [TAB] | 9 | 02100 |
| 173 | Ã | 65 | 02022 |
| 174 | ˘ | 249 | 02020 |
| 175 | [CR] | 13 | 02021 |
| 176 | ¥ | 180 | 02012 |
| 177 | , | 226 | 02001 |
| 178 | ê | 144 | 02002 |
| 179 |  | 15 | 02010 |
| 180 | 9 | 57 | 02011 |
| 181 | Ä | 128 | 02000 |
| 182 | á | 135 | 01220 |
| 183 | Ù | 243 | 01221 |
| 184 | æ | 190 | 01222 |
| 185 | œ | 207 | 01212 |
| 186 | M | 77 | 01211 |
| 187 | - | 45 | 01210 |
| 188 | [ | 91 | 01202 |
| 189 | ¿ | 192 | 01201 |
| 190 | ƒ | 186 | 01122 |
| 191 | ÿ | 216 | 01200 |
| 192 | a | 97 | 01112 |
| 193 | v | 118 | 01120 |
| 194 | ˆ | 246 | 01121 |
| 195 | ◊ | 215 | 01111 |
| 196 | 3 | 51 | 01102 |
| 197 | Œ | 206 | 01110 |
| 198 | Π | 184 | 01100 |
| 199 | " | 227 | 01101 |
| 200 | È | 233 | 01022 |
| 201 | Ì | 237 | 01021 |
| 202 | ˚ | 188 | 01020 |
| 203 | q | 113 | 01012 |
| 204 | 1 | 49 | 01011 |
| 205 | … | 201 | 01010 |
| 206 | õ | 155 | 01002 |
| 207 | fi | 222 | 01000 |
| 208 | Á | 231 | 01001 |

TABLE 1-continued

| Code Word No | 8-bit ASCII Character | Byte Value | Base 3 Coding (5 or 6 trits) |
|---|---|---|---|
| 209 |  | 5 | 00222 |
| 210 |  | 27 | 00221 |
| 211 | É | 131 | 00212 |
| 212 | § | 164 | 00220 |
| 213 |  | 3 | 00211 |
| 214 | • | 46 | 00210 |
| 215 | w | 119 | 00201 |
| 216 |  | 28 | 00202 |
| 217 | ∞ | 176 | 00200 |
| 218 |  | 23 | 00122 |
| 219 | @ | 64 | 00121 |
| 220 | ù | 157 | 00120 |
| 221 | ª | 187 | 00112 |
| 222 | Ù | 244 | 00110 |
| 223 | Ö | 238 | 00111 |
| 224 |  | 96 | 00102 |
| 225 | Î | 235 | 00101 |
| 226 | < | 60 | 00022 |
| 227 |  | 1 | 00100 |
| 228 | n | 110 | 00021 |
| 229 | » | 200 | 00011 |
| 230 | › | 221 | 00020 |
| 231 | c | 99 | 00012 |
| 232 |  | 31 | 00010 |
| 233 | Δ | 198 | 00002 |
| 234 | ¡ | 193 | 00001 |
| 235 | } | 125 | 00000 |
| 236 | \| | 124 | 22222 |
| 237 | ò | 152 | 22222 |
| 238 | z | 122 | 22222 |
| 239 | G | 71 | 222212 |
| 240 | ∧ | 94 | 222211 |
| 241 | ‹ | 220 | 222210 |
| 242 |  | 29 | 222202 |
| 243 | « | 199 | 222201 |
| 244 | = | 61 | 222200 |
| 245 |  | 11 | 222122 |
| 246 | ‰ | 228 | 222121 |
| 247 | > | 62 | 222120 |
| 248 | 7 | 55 | 222112 |
| 249 | y | 121 | 222111 |
| 250 |  | 7 | 222110 |
| 251 | - | 30 | 222102 |
| 252 | Ë | 232 | 222101 |
| 253 | Ω | 189 | 222100 |
| 254 | ; | 59 | 222021 |
| 255 | Ï | 236 | 222022 |

Encoding of the File

The arbitrary computer file 210 is represented as a string $S_\emptyset$ of bytes (often inter-preted as a number between Ø and $2^8$ 1, i.e. a value in the set {0 ... 255}). The string $S_\emptyset$ is encoded using the Huffman code and converting to base-3. This generates a string $S_1$ of characters as the trit {Ø, 1, 2}.

Let us now write len( ) for the function that computes the length (in characters) of the string $S_1$, and define $n=len(S_1)$. Represent n in base-3 and prepend 0s to generate a string $S_2$ of trits such that $len(S_2)=20$. Form the string concatenation $S_4=S_1, S_3, S_2$, where $S_3$ is a string of at most 24 zeros is chosen so that $len(S_4)$ is an integer multiple of 25.

$S_4$ is converted to the DNA string $S_5$ of characters in {A, C, G, T} with no repeated nucleotides (nt) using the scheme illustrated in the table below. The first trit of S4 is coded using the 'A' row of the table. For each subsequent trit, characters are taken from the row defined by the previous character conversion.

TABLE

Base-3 to DNA encoding ensuring no repeated nucleotides.

| previous | next trit to encode | | |
|---|---|---|---|
| nt written | Ø | 1 | 2 |
| A | C | G | T |
| C | G | T | A |
| G | T | A | C |
| T | A | C | G |

For each trit t to be encoded, select the row labeled with the previous nucleotide used and the column labeled t and encode using the nt in the corresponding table cell.

Define $N=len(S_5)$, and let ID be a 2-trit string identifying the original file and unique within a given experiment (permitting mixing of DNA form different files $S_\emptyset$ in one experiment. Split $S_5$ into the overlapping DNA segments 240 of length 100 nt, each of the DNA segments 240 being offset from the previous one of the DNA segments 240 by 25 nt. This means there will be ((N/25)−3) DNA segments 240, conveniently indexed i=Ø ... (N/25)−4. The DNA segment i is denoted $F_i$ and contains (DNA) characters 25i ... $25_{i+99}$ of $S_5$.

Each DNA segment F is further processed as follows:

If i is odd, reverse complement the DNA segment F.

Let i3 be the base-3 representation of i, appending enough leading zeros so that len(i3)=12. Compute P as the sum (mod 3) of the odd-positioned trits in ID and i3, i.e. $ID_1+i3_1+i3_3+i3_5+i3_7+i3_9+i3_{11}$. (P acts a 'parity trit'—analogous to a parity bit—to check for errors in the encoded information about ID and i.)

Form the indexing information 250 string IX=ID. i2. P (comprising 2+12+1=15 trits). Append the DNA-encoded (step 760) version of IX to $F_i$ using the same strategy as shown in the above table, starting with the code table row defined by the last character of $F_i$, to give indexed segment $F'_i$.

Form $F''_i$ by prepending A or T and appending C or G to $F'_i$—choosing between A and T, and between C and G, randomly if possible but always such that there are no repeated nucleotides. This ensures that one can distinguish a DNA segment 240 that has been reverse complemented (step 240) during DNA sequencing from one that has not. The former will start with G|C and the end with T|A; the latter will start A|T and end C|G.

The segments $F''_I$ are synthesized in step 790 as actual DNA oligonucleotides and stored in step 790 and may be supplied for sequencing in step 820.

Decoding

Decoding is simply reverse of the encoding in step 720, starting with the sequenced DNA segments 240 $F''_I$ of length 117 nucleotides. Reverse complementation during the DNA sequencing procedure (e.g. during PCR reactions) can be identified for subsequent reversal by observing whether fragments start with A|T and end with C|G, or start with G|C and end T|A. With these two 'orientation' nucleotides removed, the remaining 115 nucleotide of each DNA segment 240 can be split into the first 100 'message' nucleotides and the remaining fifteen 'indexing information 250' nucleotides. The indexing information nucleotide 250 can be decoded to determine the file identifier ID and the position index i3 and hence i, and errors may be detected by testing the parity trit P. Position indexing information 250 permits the reconstruction of the DNA-encoded file 230, which can then be converted to base-3 using the reverse of the encoding table above and then to the original bytes using the given Huffman code.

Discussion on Data Storage

The DNA storage has different properties from the traditional tape-based storage or disk-based storage. The ~750 kB of information in this example was synthesized in 10 pmol of DNA, giving an information storage density of approximately one Terabyte/gram. The DNA storage requires no power and remains (potentially) viable for thousands of years even by conservative estimates.

DNA Archives can also be copied in a massively parallel manner by the application of PCR to the primer pairs, followed by aliquoting (splitting) the resulting DNA solution. In the practical demonstration of this technology in the sequencing process this procedure was done multiple times, but this could also be used explicitly for copying at large scale the information and then physically sending this information to two or more locations. The storage of the information in multiple locations would provide further robustness to any archiving scheme, and might be useful in itself for very large scale data copying operations between facilities.

The decoding bandwidth in this example was at 3.4 bits/second, compared to disk (approximately one Terabit/second) or tape (140 Megabit/second), and latency is also high (~20 days in this example). It is expected that future sequencing technologies are likely to improve both these factors.

Figure 3:
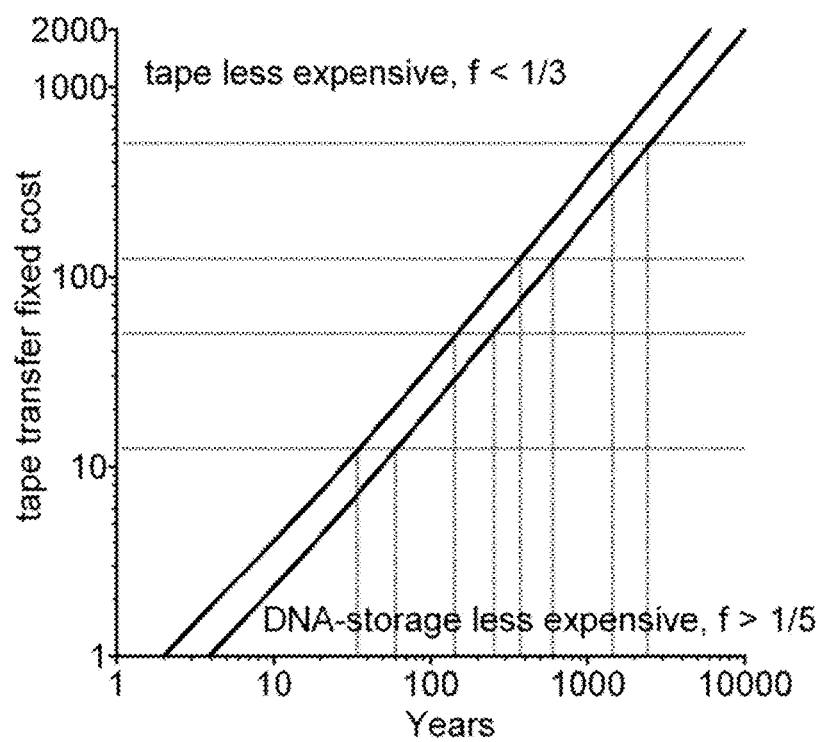
FIG. 3 shows a graph of the cost effectiveness of storage over time.

Modeling the full cost of archiving using either the DNA-storage of this disclosure or the tape storage shows that the key parameters are the frequency and fixed costs of transitioning between tape storage technologies and media. FIG. 3 shows the timescales for which DNA-storage is cost-effective. The upper bold curve indicates the break-even time (x-axis) beyond which the DNA storage as taught in this disclosure is less expensive than tape. This assumes that the tape archive has to be read and re-written every 3 years (f=⅓), and depends on the relative cost of DNA-storage synthesis and tape transfer fixed costs (y-axis). The lower bold curve corresponds to tape transfers every 5 years. The region below the lower bold curve indicates cases for which the DNA storage is costeffective when transfers occur more frequently than every 5 years; between the two bold curves, the DNA storage is cost-effective when transfers occur from 3- to 5-yearly; and above the upper bold curve tape is less expensive when transfers occur less frequently than every 3 years. The dotted horizontal lines indicate ranges of relative costs of DNA synthesis to tape transfer of 125-500 (current values) and 12.5-50 (achieved if DNA synthesis costs reduce by an order of magnitude). Dotted vertical lines indicate corresponding break-even times. Note the logarithmic scales on all axes.

One issue for long-term digital archiving is how DNA-based storage scales to larger applications. The number of bases of the synthesized DNA needed to encode the information grows linearly with the amount of information to be stored. One must also consider the indexing information required to reconstruct full-length files from the short DNA segments 240. The indexing information 250 grows only as the logarithm of the number of DNA segments 240 to be indexed. The total amount of synthesized DNA required grows sub-linearly. Increasingly large parts of each ones of the DNA segments 240 are needed for indexing however and, although it is reasonable to expect synthesis of longer strings to be possible in future, the behavior of the scheme was modeled under the conservative constraint of a constant 114 nucleotides available for both the data and the indexing information 250.

As the total amount of information increases, the encoding efficiency decreases only slowly (FIG. 5). In the experiment (megabyte scale) the encoding scheme is 88% efficient. FIG. 5 indicates that efficiency remains >70% for data storage on petabyte (PB, $10^{15}$ bytes) scales and >65% on exabyte (EB, $10^{18}$ bytes) scales, and that DNA-based storage remains feasible on scales many orders of magnitude greater than current global data volumes. FIG. 5 also shows that costs (per unit information stored) rise only slowly as data volumes increase over many orders of magnitude. Efficiency and costs scale even more favourably if we consider the lengths of the synthesized DNA segments 240 available using the latest technology. As the amount of information stored increases, decoding requires more oligos to be sequenced. A fixed decoding expenditure per byte of encoded information would mean that each base is read fewer times and so is more likely to suffer decoding error. Extension of the scaling analysis to model the influence of reduced sequencing coverage on the per-decoded-base error rate revealed that error rates increase only very slowly as the amount of information encoded increases to a global data scale and beyond. This also suggests that the mean sequencing coverage of 1,308 times was considerably in excess of that needed for reliable decoding. This was confirmed by subsampling from the $79.6 \times 310^6$ read-pairs to simulate experiments with lower coverage.

FIG. 5 indicates that reducing the coverage by a factor of 10 (or even more) would have led to unaltered decoding characteristics, which further illustrates the robustness of the DNA-storage method. Applications of the DNA-based storage might already be economically viable for long-horizon archives with a low expectation of extensive access, such as government and historical records. An example in a scientific context is CERN's CASTOR system, which stores a total of 80 PB of Large Hadron Collider data and grows at 15 PB $yr^{-1}$. Only 10% is maintained on disk, and CASTOR migrates regularly between magnetic tape formats. Archives of older data are needed for potential future verification of events, but access rates decrease considerably 2-3 years after collection. Further examples are found in astronomy, medicine and interplanetary exploration.

FIG. 5 shows the encoding efficiency and costs change as the amount of stored information increases. The x-axis (logarithmic scale) represents the total amount of information to be encoded. Common data scales are indicated, including the three zettabyte (3 ZB, $3 \times 10^{21}$ bytes) global data estimate. The y-axis scale to left indicates encoding efficiency, measured as the proportion of synthesized bases available for data encoding. The y-axis scale to right indicate the corresponding effect on encoding costs, both at current synthesis cost levels (solid line) and in the case of a two-order-of magnitude reduction (dashed line).

Figure 6:
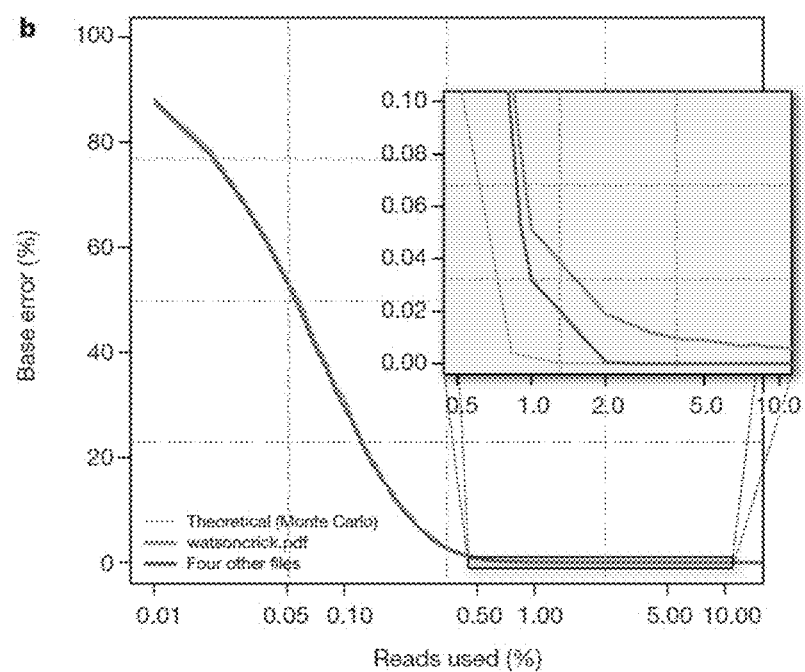
FIG. 6 shows error rates.

FIG. 6 shows per-recovered-base error rate (y-axis) as a function of sequencing coverage, represented by the percentage of the original $79.6 \times 10^6$ read-pairs sampled (x axis; logarithmic scale). One curve represents the four files recovered without human intervention: the error is zero when ≥2% of the original reads are used. Another curve is obtained by Monte Carlo simulation from our theoretical error rate model. The final curve represents the file (watsoncrick.pdf) that required manual correction: the minimum possible error rate is 0.0036%. The boxed area is shown magnified in the inset.

In addition to data storage, the teachings of this disclosure can also be used for steganography.

What is claimed is:

1. A method of storing an item of information in a plurality of DNA segments, the method comprising:
   encoding bytes in an item of information stored in a first computer file as a DNA sequence data using a representation schema to represent the encoded bytes as at least one DNA nucleotide datum in the DNA sequence data;
   splitting the DNA sequence data into a plurality of overlapping DNA segments data, wherein the plurality of overlapping DNA segments data build in a redundancy of storage of the items of information;
   adding indexing information to the plurality of DNA segments data, the indexing information indicating a position in the DNA sequence data of any one nucleotide datum in any one of the plurality of DNA segments data;
   synthesizing, by providing the plurality of DNA segments data as input to a computer-controlled DNA synthesis platform, a plurality of DNA segments.

2. The method of claim 1, further including the addition of adapters data to the DNA segments data.

3. The method of claim 1 using a base-3 scheme for encoding the bytes.

4. The method of claim 1, wherein the representation schema used is designed such that adjacent ones of the DNA nucleotide data are different.

5. The method of claim 1, further comprising adding a parity-check to the indexing information.

6. The method of claim 1, wherein alternate ones of the DNA segments data are reverse complemented.

7. The method of claim 1, wherein the representation schema used is designed to avoid long, self-reverse complementary DNA segments data.

8. The method of claim 1, further comprising:
   storing the synthesized DNA segments in one or more DNA archives.

9. A plurality of DNA segments that store an item of information, wherein the plurality of DNA segments data are produced by a method comprising:
   encoding bytes in an item of information, stored in a first computer file, as a DNA sequence data using a representation schema to represent the encoded bytes as at least one DNA nucleotide datum in the DNA sequence data;
   splitting the DNA sequence data into a plurality of overlapping DNA segments data, wherein the plurality of overlapping DNA segments data build in a redundancy of storage of the items of information;
   augmenting indexing information to the plurality of DNA segments data, the indexing information indicating a position in the DNA sequence data of any one nucleotide datum in any one of the plurality of DNA segments data; and
   synthesizing, by providing the plurality of DNA segments data as input to a computer-controlled DNA synthesis platform, a plurality of DNA segments.

* * * * *